United States Patent
Lemonis

(10) Patent No.: US 10,086,470 B2
(45) Date of Patent: Oct. 2, 2018

(54) METHOD FOR ENERGY CALIBRATION OF A PULSED CUTTING LASER FOR EYE SURGERY

(71) Applicant: Wavelight GmbH, Erlangen (DE)

(72) Inventor: Sissimos Lemonis, Erlangen (DE)

(73) Assignee: Wavelight GmbH (DE)

( * ) Notice: Subject to any disclaimer, the term of this patent is extended or adjusted under 35 U.S.C. 154(b) by 456 days.

(21) Appl. No.: 15/081,392

(22) Filed: Mar. 25, 2016

(65) Prior Publication Data

US 2016/0325375 A1 Nov. 10, 2016

(30) Foreign Application Priority Data

May 6, 2015 (DE) ........................ 10 2015 005 820

(51) Int. Cl.
| | |
|---|---|
| *B23K 26/06* | (2014.01) |
| *B23K 26/00* | (2014.01) |
| *B23K 26/03* | (2006.01) |
| *A61F 9/00* | (2006.01) |
| *B23K 26/0622* | (2014.01) |
| *A61F 9/008* | (2006.01) |

(52) U.S. Cl.
CPC ........ *B23K 26/0622* (2015.10); *A61F 9/0084* (2013.01); *A61F 9/00814* (2013.01); *B23K 26/0006* (2013.01); *B23K 26/03* (2013.01); *A61F 2009/00855* (2013.01)

(58) Field of Classification Search
CPC ........ B23K 26/06; B23K 26/00; B23K 26/03; A61F 9/00
USPC ........................ 219/121.61, 121.69; 264/400
See application file for complete search history.

(56) References Cited

U.S. PATENT DOCUMENTS

| | | | |
|---|---|---|---|
| 4,713,537 A | 12/1987 | Kunz et al. | |
| 8,687,178 B2 | 4/2014 | Deisinger et al. | |
| 9,034,539 B2 * | 5/2015 | Oshemkov | ............ G03F 7/2002 430/33 |
| 2003/0189031 A1 | 10/2003 | Troitski et al. | |
| 2009/0137988 A1 | 5/2009 | Kurtz | |
| 2009/0149841 A1 | 6/2009 | Kurtz | |
| 2010/0324543 A1 | 12/2010 | Kurtz et al. | |

FOREIGN PATENT DOCUMENTS

| | | |
|---|---|---|
| EP | 2826447 A2 | 1/2015 |
| WO | 94/25836 A1 | 11/1994 |
| WO | 2012/041346 A1 | 4/2012 |

* cited by examiner

*Primary Examiner* — Samuel M Heinrich
(74) *Attorney, Agent, or Firm* — Keiko Ichiye, Esq.

(57) ABSTRACT

A method for energy calibration of a pulsed cutting laser for eye surgery comprises irradiating a sample material with a plurality of sets of laser pulses of the cutting laser with pulse energies differing from set to set. This method also comprises analyzing at least one visually perceptible discoloration structure created in the sample material as a result of the irradiation, selecting the pulse energy of one of the sets based on the analysis, and setting a treatment pulse energy for the cutting laser based on the selected energy.

19 Claims, 3 Drawing Sheets

METHOD FOR ENERGY CALIBRATION OF A PULSED CUTTING LASER FOR EYE SURGERY

CROSS REFERENCE TO RELATED APPLICATIONS

This application claims priority to German Patent Application Serial Number 102015005820.7, filed 6 May 2015, titled "METHOD FOR ENERGY CALIBRATION OF A PULSED CUTTING LASER FOR EYE SURGERY," which is hereby incorporated by reference in its entirety.

TECHNICAL FIELD

The present disclosure relates in general to energy calibration of a pulsed cutting laser. It relates in particular to energy calibration of a pulsed cutting laser for eye surgery, this laser being suitable for technical laser production of cuts in tissue of an eye, for example, in a human cornea or in lens tissue.

BACKGROUND

In a number of different surgical procedures it is necessary to make cuts in an eye. To name just two examples, cuts are made in corneal tissue as part of a so-called LASIK surgery (LASIK: laser in-situ keratomileusis) in preparation for a corneal flap, as it is often referred to in English terminology, or as part of an intracorneal lenticule extraction for separation of a volume of corneal tissue, which is then removed from the cornea. Laser equipment has recently been developed to make it possible to create such cuts using laser technology.

The physical effect of the so-called laser-induced optical breakdown is utilized in creating cuts by means of focused laser radiation in transparent or translucent material (transparent/translucent for the laser radiation). The penetration leads to a photodisruption of the irradiated tissue in the region of the focus of the laser radiation. The interaction of the incident laser radiation with the irradiated corneal tissue causes a local evaporation of tissue at the focal point. To ensure a reproducible, high-quality cut, the properties of the laser must be checked at sufficiently short intervals of time and readjusted, if necessary. An important factor here is the pulse energy of the pulsed cutting laser being used. To ensure a high-quality cut, the energy actually incident on the surface of the cut must be known and adjustable accordingly. If the pulse energy is too low, it may result in the cut being too deep and/or not efficient enough. If the pulse energy is too high, it may result in the cut not being deep enough and/or too wide and may thus lead to unwanted damage to neighboring tissue. Over a period of time, the pulse energy that is actually incident upon a cut surface may deviate from the pulse energy set on the cutting laser. In the prior art, a calibration is therefore performed at regular intervals, so that an energy measuring device (for example, a conventional power meter) can be used to determine the power and/or pulsed energy actually incident upon the cutting surface and to adjust the pulse energy set on the cutting laser accordingly.

However, it has been found that the result of the photodisruption (for example, the size of the gas bubbles produced) does not depend only on the amount of incident energy but is also influenced by other factors such as, for example, the beam diameter, the pulse length, the energy control of the device, etc. The cutting result to be expected may vary if one of the aforementioned factors changes during production (e.g., due to production spread) or during use of the cutting laser.

The final cutting result is achieved by a combination of incident laser light dose and placement of pulses which are arranged in a spiral or linear arrangement. The cutting effect and the respective settings for use on human corneal tissue depend to a high degree on each of the aforementioned factors. A change in any of the factors will change the cutting process per se. The dose is usually adjusted by varying the energy and if this is not sufficient the cutting pattern is rearranged in a narrower or more controlled manner. Nevertheless the total dose of the incident laser beams may have serious effects on the quality of the flap or may cause corneal reactions such as inflammation, DLK, haze, etc.

SUMMARY OF EXEMPLARY EMBODIMENTS

One object of the present invention is to avoid the problems mentioned above and to provide a method for energy calibration of a cutting laser which takes into account as many factors as possible which contribute to the quality of a cut that is created.

One aspect of the present invention is a method for energy calibration of a pulsed cutting laser for eye surgery, comprising: irradiating a sample material with a plurality of sets of laser pulses of the cutting laser with pulse energies differing from set to set; analyzing at least one visually perceptible discoloration structure created in the sample material as a result of the irradiation; selecting the pulse energy of one of the sets based on the analysis; and setting a treatment pulse energy for the cutting laser based on the selected energy.

The irradiation of a sample material leads to photodisruption in the sample material when the pulse energy used exceeds a certain threshold value. The photodisruption causes a visually perceptible discoloration structure (for example, a blackening) in the sample material. This discoloration structure can be detected visually (with the eye) or with the help of at least one optical device, for example. During the irradiation of the sample material, the cutting laser may trace over a certain uniform pattern (for example, a circle, an ellipse, a line, a rectangle, etc.) for each set of laser pulses. In this way, a visually perceptible discoloration structure can be created for each of the sets of laser pulses whose pulse energy is above the threshold value for the photodisruptive effect in the sample material. The discoloration structures may have essentially the same pattern as seen from above. This simplifies a (optical) comparison between the different discoloration structures and thus analysis of the at least one discoloration structure. The different pulse energies of the multiple sets of laser pulses can be set by hand, for example, by a user of the cutting laser or may be set automatically by a control unit. The treatment pulse energy may be set so that it corresponds to the product of the selected energy multiplied times a certain factor, for example.

The sample material may be transparent.

The sample material may be transparent for the visible optical wavelength spectrum, for example. By supplying a transparent sample material, a discoloration structure caused by the cutting laser can be perceived visually easily. This facilitates the analyzing step. The transparent sample material may be or comprise PMMA, for example.

The sets may each be irradiated at different regions of the sample material.

The sample material may have a surface, for example, wherein the different sets are irradiated into different regions of the surface. The sets may leave behind a discolored structure in the various regions. The sample material may be in the form of a plate, for example. The sample material may be designed like a plate.

The various regions of the sample material can be separated from one another by visible marks.

The separation may be embodied, for example, by perforation of a surface of the sample material. In this way the individual regions of the sample material can easily be differentiated from one another visually, which facilitates the analysis of the at least one discoloration structure.

The sample material may be provided with written indications, which define a pulse energy in local assignment for each one of the regions.

For example, precisely one item of written indication may be provided for the pulse energy for each of the different regions. The written indication may be provided in the respective region, for example. The respective values for the pulse energy may correspond to the energies set on the cutting laser for irradiation of the respective region.

A plate-type piece of material made, for example, of PMMA may be used as the sample material and the sets may each be irradiated at different plate regions of the piece of material.

The plate-type piece of material may be subdivided into the various plate regions in the form of a matrix, for example. Precisely one plate region may be provided for each of the sets, with the respective set of laser pulses being irradiated into that region.

Each one of the sets may correspond to a nominal geometric figure, and the pulse energy of such a set may be selected, at which a discoloration structure is created in the sample material, which completely represents the nominal geometric figure.

The discoloration structure, which completely represents the nominal geometric figure may be, for example, a discoloration structure having a continuous discoloration. The nominal geometric figure may be traced by the cutting laser during irradiation by the respective set.

The nominal geometric figure may be or comprise a line figure.

The discoloration structure, which completely represents the nominal geometric figure may be, for example, a discoloration structure, which has a completely continuous line of discoloration along the nominal geometric figure.

The line figure may be closed in the form of a ring.

The line figure may comprise and/or represent, for example, a circle, an ellipse or a rectangle.

The pulse energy of the set having the lowest pulse energy may be selected, at which a discoloration structure is created in the sample material, which completely represents the nominal geometric figure.

The pulse energy of such a set may be selected, at which needle-like discoloration structures, which are created in the sample material as a result of the irradiation with the set, satisfy at least a certain size condition.

The needle-like discolorations may be oriented in the sample material in such a way that a longitudinal axis of the needle-like discoloration structures extends along an incident direction of the cutting laser. The size condition of the needle-like discoloration structures can be determined visually, for example. The size condition may be, for example, a minimum diameter, a minimum length or a combination of these two criteria.

A size condition may be the fact that a needle length of the needle-like discoloration structures amounts to at least a given reference length.

Analysis of the at least one discoloration structure may include the measurement of needle lengths of the needle-like discoloration structures. The needle lengths can be measured visually, for example. If the sample material is a plate-type sample material, the needle-like discoloration structures may be aligned along a thickness direction of the plate-type sample material, for example, and the needle-like discoloration structures can be analyzed by considering a cross section of the plate-type sample material.

A size condition may be the fact that at least a subset of the needle-like discoloration structures each has a needle length amounting to at least a given reference length.

The subset may be a number set previously. Random extreme values of the needle lengths can be disregarded by considering a subset. This can increase the reliability of the analysis.

This method may also include optically detecting the at least one discoloration structure by using a camera.

The camera may be a digital camera. The camera may have, for example, a CCD or CMOS sensor for detecting an image of the discoloration structure. An enlargement apparatus may be connected upstream from the camera. The enlargement apparatus may be a combination of collecting lenses and/or scattering lenses, for example. The camera may be connected to an analysis apparatus. The analysis apparatus may be part of a control unit of the cutting laser. Further, a light source may be provided for illuminating the sample material and the discoloration structure. The light source may be configured to emit light only in a defined frequency band and/or to sequentially emit light in different defined frequency bands. Therefore, at least one suitable filter may be provided.

This method may also include displaying of a camera image on a display screen, the camera image showing the at least one discoloration structure.

The display screen may be designed so that it can be observed by a user of the cutting laser. The camera image may be processed by software based on optical filters. The camera image may comprise an enlarged region of the discoloration structure. The camera image may also comprise a true-to-scale length scale for measuring the extent of the discoloration structure in at least one dimension.

The analysis may comprise a software-assisted analysis of a camera image showing the at least one discoloration structure.

The software-assisted analysis may be performed with the help of a control unit of the cutting laser, for example. The software-assisted analysis may include the measurement of the extent of the discoloration structure in at least one dimension. The software-assisted analysis may include a comparison of the discoloration structure with a reference structure.

The laser pulses may have a pulse duration in the range of atto-, femto- or picoseconds.

The method may also include: determining a measured pulse energy of the cutting laser by means of an energy meter; and adjusting, based on the measured pulse energy, a scale of an energy value displayed at the cutting laser as instantaneous energy, such that subsequently the energy value displayed at the cutting laser as instantaneous energy corresponds to an actual pulse energy.

The pulse energy of the cutting laser can be measured by a commercial power meter, for example, whose sensor is located either in the main path of the beam of the cutting laser (for example, in situ on the sample material) or in a beam path, which is diverted by a beam splitter. The measured pulse energy of the cutting laser corresponds to the actual pulse energy of the cutting laser at the point in time of the measurement. An energy calibration can be achieved by adapting the scale. The energy value displayed as the instantaneous energy may be an energy value, which is displayed for a user of the cutting laser, for example, while the user is adjusting an energy value, which is instantaneously (currently) set as the pulse energy on the cutting laser. By adjusting the scale, it is possible to achieve the result that a correct energy value, which corresponds to the actual pulse energy, is displayed for the user of the cutting laser. For example, a measured pulse energy may be determined for several energy values set as pulse energy on the cutting laser. The adjustment may be made on the basis of the plurality of measured pulse energy values. It is thus possible to achieve the result that by calibration of the pulse energy, the incident energy of the cutting laser on a sample is known.

This method may also include: determining a ratio between a known reference energy value for the creation of a desired discoloration structure and the selected energy; determining an effective energy as the product of an energy value currently set as pulse energy at the cutting laser and the ratio; and displaying the effective energy to a user of the cutting laser, wherein the step of setting is carried out based on the effective energy.

The reference energy value may be, for example, a pulse energy, which is known to have previously led reliably to an adequate discoloration structure in a comparable sample material. The energy value set currently as the pulse energy on the cutting laser may be an actual pulse energy of the cutting laser, for example. This may be determined in advance by calibration using a power meter. The effective energy may be displayed for the user, for example, simultaneously with the currently set energy value. The effective energy can be displayed for the user, for example, while the user is changing the pulse energy of the cutting laser. The setting step may be made on the basis of the effective energy, for example, so that a predetermined effective energy is selected as the treatment pulse energy. By displaying the effective energy, it is possible to ensure that an energy scale (effective energy) is always displayed for the user of the cutting laser, such that the setting at the same effective energy value leads to a comparable cutting result and/or a comparable photodisruption in a sample material or in the human cornea. In other words, an energy (effective energy) may be displayed to the user of the cutting laser, which allows conclusions regarding the result of photodisruption to be expected.

BRIEF DESCRIPTION OF THE DRAWINGS

Supplementary features, advantages and components of the present invention can be derived from the following description of the accompanying drawings, in which.

DETAILED DESCRIPTION OF EXEMPLARY EMBODIMENTS

Figure 1:
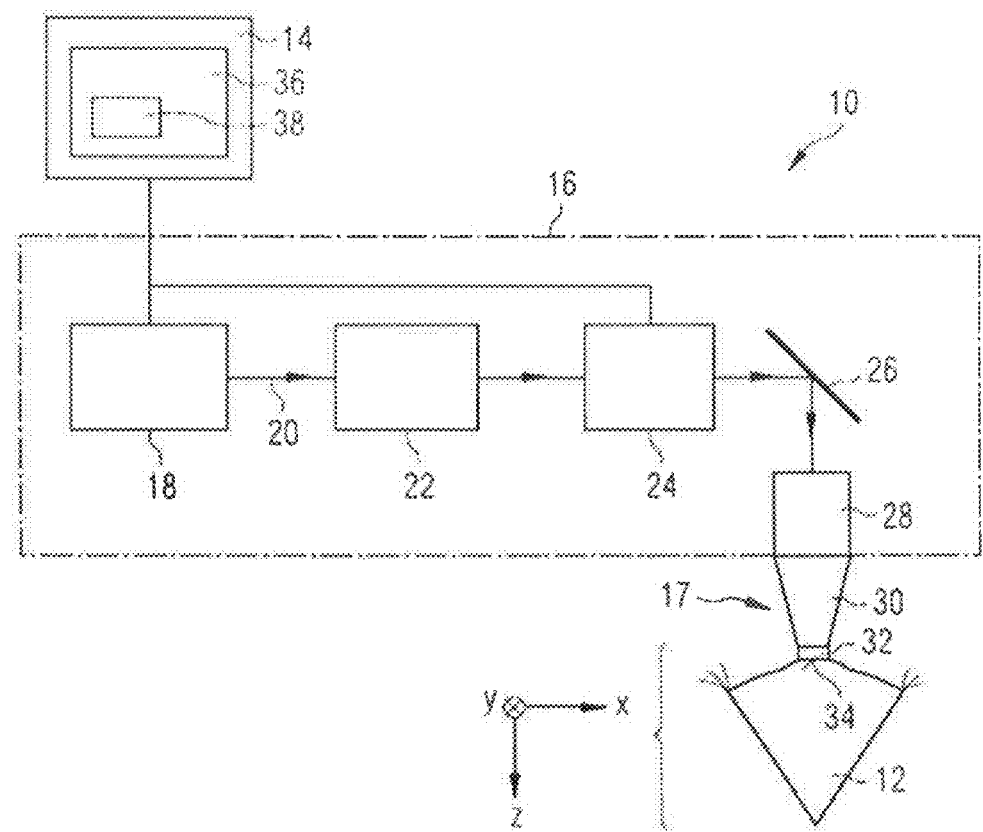
FIG. 1 shows a schematic block diagram of a device known from the prior art for laser processing of a human eye.

FIG. 1 shows in a block diagram an exemplary device from the prior art, which is labeled as 10 in general, for laser processing of a human eye 12. The device 10 comprises a control unit 14, a laser arrangement 16 and a patient adapter 17. The device 10 is an example of a pulsed cutting laser, which can be calibrated by the method according to the invention.

The laser arrangement 16 comprises a laser source 18 which generates a laser beam 20 having pulse durations in the femtosecond range, for example. The laser beam 20 has a suitable wavelength for generating a laser-induced optical breakdown in the corneal tissue of the eye 12. The laser beam 20 may have a wavelength in the range of 300 nm (nanometer) to 1900 nm, for example, a wavelength in the range of 300 nm to 650 nm, 650 nm to 1050 nm, 1050 nm to 1250 nm or 1100 nm to 1900 nm. The laser beam 20 may also have a focus diameter of 5 µm or less.

Behind the laser source 18 in the direction of propagation of the laser beam 20 (indicated by the arrows in FIG. 1) a beam widening optical system 22, a scanner unit 24, a mirror 26 and a focusing lens 28 are arranged. The beam widening optical system 22 serves to enlarge the diameter of the laser beam 20 generated by the laser source 18. In the example shown here, the beam widening optical system 22 is a Galileo telescope, comprising a concave lens (lens having a negative refractive power) and a convex lens (lens having a positive refractive power) situated downstream from the concave lens in the direction of propagation of the laser beam 20. This may be a planar concave lens and a planar convex lens whose planar sides are arranged so they face one another. In another example, the beam widening optical system may comprise, for example, a Kepler telescope, which has two convex lenses, as an alternative to a Galileo telescope.

The scanner unit 24 is designed to control the position of the focus of the laser beam 20 (beam focus) in the transverse direction and in the longitudinal direction. The transverse direction describes the direction across the direction of propagation of the laser beam 20 (characterized as the x-y plane) and the longitudinal direction describes the direction of propagation of the laser beam 20 (characterized as the z direction). The scanner unit 24 may comprise, for example, a pair of galvanometrically actuated deflecting mirrors, which can be tilted about mutually orthogonal axes, for transverse deflection of the laser beam 20. Alternatively or additionally, the scanner unit 24 may have an electrooptical crystal or other components suitable for transverse deflection of the laser beam 20. The scanner unit 24 may also comprise a lens that is adjustable longitudinally or has a variable refractive power or may comprise a deformable mirror to influence the divergence of the laser beam 20 and, consequently, the longitudinal alignment of the beam focus. In the example shown here, the components for control of the transverse orientation and longitudinal orientation of the beam focus are depicted as integral components. In another example, the components may be arranged separately along the direction of propagation of the laser beam 20. Thus, an adjustable mirror, for example, may be arranged in front of the beam widening optical system 22 in the direction of propagation, for control of the longitudinal orientation of the beam focus.

The mirror 26 may be a stationary deflecting mirror, which is designed to deflect the laser beam 20 in the direction of the focusing lens 28. Additionally or alternatively, other optical mirrors and/or optical elements may be arranged in the beam path for deflecting and diffracting the laser beam 20.

The focusing lens 28 is designed to focus the laser beam 20 on the region of the cornea of the eye 12 to be processed. The focusing lens 28 may be, for example, an F-theta lens. The focusing lens 28 is releasably connected to the patient adapter 17. The patient adapter 17 comprises a conical carrier sleeve 30, which is connected to the focusing lens 28 by means of a coupling formation (not shown), and a contact element 32 which is attached to the narrower bottom side of the carrier sleeve 30 facing the eye 12. The contact element 32 may be attached to the carrier sleeve 30 either releasably (for example, by screw connection) or permanently (e.g., by adhesive bonding). The contact element 32 has a bottom side which faces the eye 12 and is characterized as a contact face 34. The contact face 34 in the example shown here is embodied as a flat surface. In laser processing of the eye 12 the contact element 32 is pressed against the eye 12 or the eye 12 is drawn to the contact surface 34 by vacuum suction, such that at least the region of the cornea of the eye 12 to be processed is leveled.

The control unit 14 comprises a memory 36, in which at least one control program 38 having program instructions is stored. The laser source 18 and the scanner unit 24 are controlled by the control unit 14 in accordance with the program instructions. The control program 38 includes program instructions, which, when executed by the control unit 14, produce a movement of the beam focus in space and time, such that a cutting figure is created in the cornea of the eye 12 to be treated.

Figure 2:
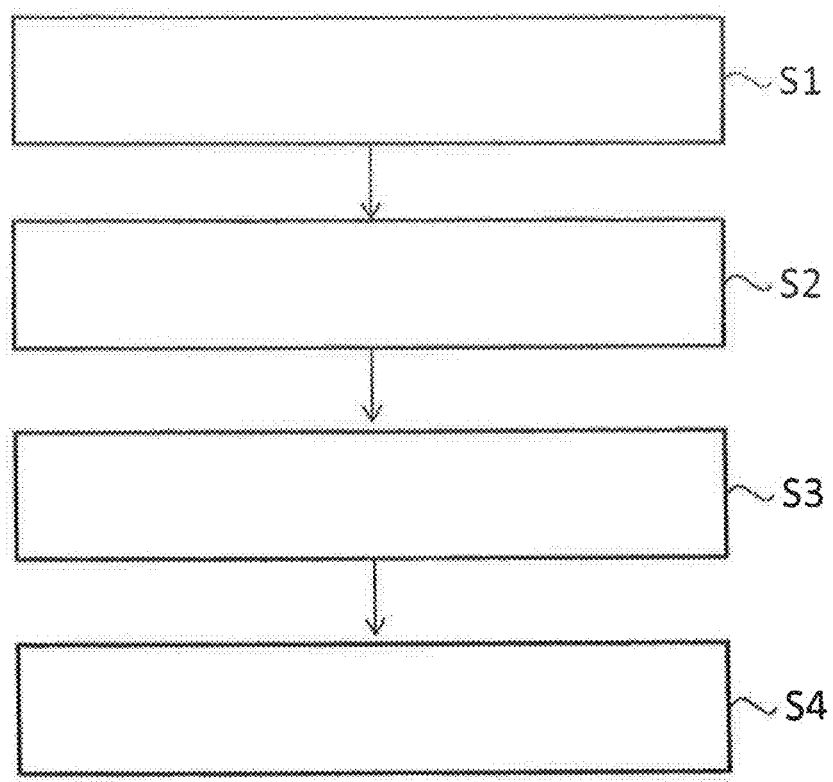
FIG. 2 shows a flow chart for an exemplary embodiment of a method according to the invention.

FIG. 2 shows a flow chart for an exemplary embodiment of a method according to the invention for energy calibration of a pulsed cutting laser for eye surgery. The pulsed cutting laser may be, for example, the device 10 shown in FIG. 1.

The method for energy calibration of a pulsed cutting laser for eye surgery comprises at least the following steps S1-S4:

Irradiating S1 a sample material with a plurality of sets of laser pulses of the cutting laser with pulse energies differing from set to set;

Analyzing S2 at least one visually perceptible discoloration structure created in the sample material as a result of the irradiation;

Selecting S3 the pulse energy of one of the sets based on the analysis; and

Setting S4 a treatment pulse energy for the cutting laser based on the selected energy.

According to the exemplary embodiment, the steps S1, S2, S3 and S4 mentioned above are performed in this order.

Figure 3A:
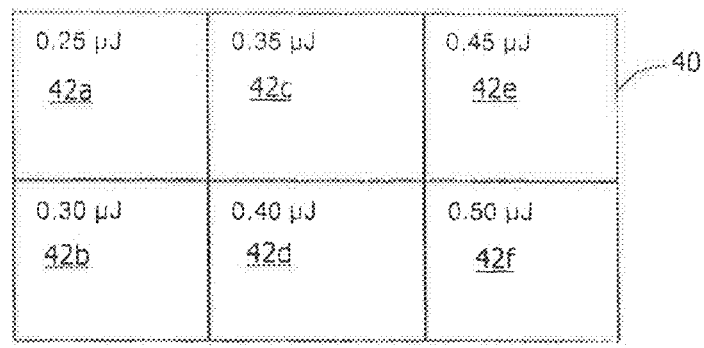
FIG. 3A shows a schematic top view of an exemplary embodiment of a sample material which can be used for a method according to the invention.

FIG. 3A shows an exemplary embodiment of a sample material 40 which is subdivided visibly (for example, due to printing or perforation) into a plurality of regions 42a-42f. The individual regions 42a-42f are delimited from one another by visible marks. Each of the regions 42a-42f is characterized by written notation of a nominal energy value (0.25 µJ, 0.30 µJ, 0.35 µJ, etc.). FIG. 3A shows the sample material 40 in a view from above, so that the plane of the drawing is parallel to the x-y plane when the sample material 40 is used with the cutting laser from FIG. 1. According to one exemplary embodiment, the sample material 40 may be a thin plate of PMMA.

According to one exemplary embodiment, the method for energy calibration of the pulsed cutting laser is carried out with the help of the sample material 40, so that a first energy value for the pulse energy (for example, 0.25 µJ) is set first on a setting device of the cutting laser.

The setting device may optionally first be calibrated with the help of a power meter so that an energy value set on the cutting laser corresponds to an energy value measured by the power meter. The calibration may be necessary because the cutting laser can become decalibrated, so that a displayed energy value that has been set on the cutting laser no longer corresponds to the actual pulse energy. Due to the calibration, it is possible to achieve the result that the actual pulse energy of the cutting laser is always displayed for the user when an energy value is being set.

This may be accomplished by adjusting a scale of an energy value displayed as the instantaneous energy on the cutting laser. A sensor of the power meter (for example, a commercial power meter) may be arranged either in the main beam path of the cutting laser or in a secondary beam path branching off through a beam splitter (with a known splitting ratio) for measuring the power.

The sample material 40 is irradiated with the cutting laser from above (perpendicular to the plane of the drawing in the representation of FIG. 3A), whereupon the pulse energy of the cutting laser is set at the first energy value. A certain nominal geometric figure is traced hereby (for example, a line, a wavy line, a circle, a rectangle, an ellipse, etc.) by the cutting laser in the region 42a which is indicated by the corresponding energy. The nominal geometric figure may be a line figure, for example, which may be closed in the form of a ring (circle, rectangle, ellipse, etc.). The nominal geometric figure may also have at least one meandering region. Depending on the pulse energy of the cutting laser and other properties, such as the pulse duration, the beam widening at the focal point and/or the position of the focal point relative to the sample material 40, there is already photodisruption and discoloration in the sample material 40 with the first energy. The discoloration created in a respective region of the sample material 40 at a certain pulse energy is referred to below as a discoloration structure. It may be that, at the low first energy level set, either no discoloration structure at all is created or it is not continuous, so there are gaps in the discoloration structure in comparison with the nominal geometric figure.

Next, the pulse energy of the cutting laser is set at a second energy value (for example, 0.30 µJ) and a second region 42b of the sample material 40 is traced with this energy and the same pattern as before. Additional regions 42c-f of the sample material 40 are then irradiated successively with sets of laser pulses of a corresponding pulse energy, wherein the irradiation pattern remains the same for each of the regions 42a-f.

Alternatively, it is possible to trace only one large pattern, for example, wherein the pulse energy of the cutting laser is increased incrementally while tracing the pattern. Furthermore, any sequence of the set energies may be used and it is also possible to begin with a high energy, for example, and then gradually reduce it in the course of the method.

Next, the visually perceptible discoloration structures created in the sample material 40 due to the irradiation are analyzed. The plurality of discoloration structures consists of the individual discoloration structures of the various regions 42a-f and thus includes at least one discoloration structure. The analysis may be performed with the naked eye, for example, or with the eye and an optical aid such as a microscope or a magnifying glass. However, it is also possible to use a camera with a corresponding magnification lens for the analysis. If the analysis is performed in a view from above, it is possible to analyze which of the discoloration structures are sufficiently continuous, for example, and which are not (for example, if they have gaps or if the discoloration is too thin). The discoloration structures produced can therefore be compared with the nominal geometric figures. For example, it is possible to determine which of the discoloration structures correspond to the nominal geometric figure and which have gaps and/or an incomplete discoloration.

Figure 3B:
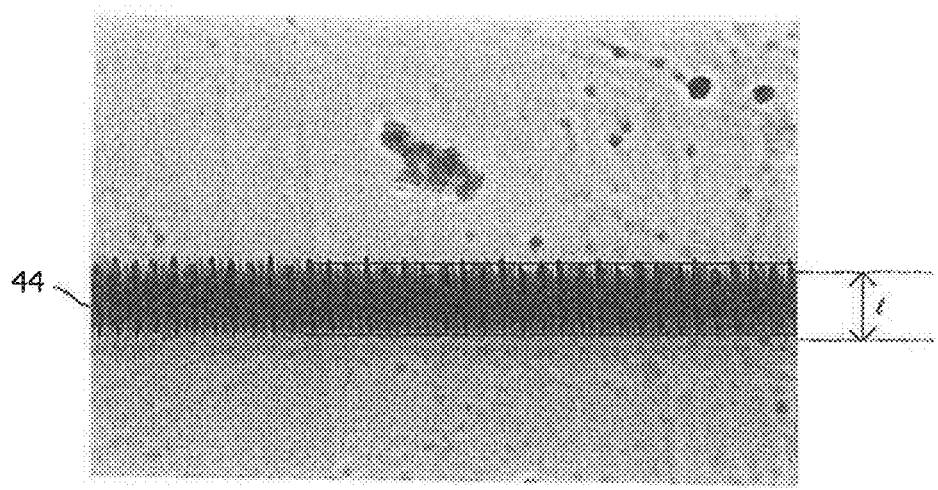
FIG. 3B shows an exemplary side view of discoloration structure needles in a sample material.

Alternatively or additionally, as shown in FIG. 3B, the analysis may be performed in a side view of the sample material 40. FIG. 3B shows a side view of the sample material 40, for example, the sample material 40 shown in FIG. 3A. When the analysis is performed by considering a side view, it may be beneficial to irradiate the sample material only in an edge region of the sample material. Thus, the discoloration structures may be viewed in side view without cutting or breaking the sample material in advance. Therefore, for example, a polygon may be used, the side edges of which are irradiated by the cutting laser with different pulse energies.

As shown in FIG. 3B, the pulsed laser beam has left behind a plurality of needle-like discoloration structures (discoloration structure needles) in the sample material 40 due to photodisruption. The needle-like discoloration structures are oriented in the sample material 40 along the incident direction of the cutting laser (z direction in FIG. 1), wherein their length l varies along this incident direction, depending on the pulse energy and beam quality (diameter and pulse duration, respectively) of the cutting laser used with the cutting laser.

For a certain pulse energy, the needle-like discoloration structures have a characteristic length l, which increases with an increase in the pulse energy. For example, the length l of the needle-like discoloration structures can be determined visually (with a user's eye) using a suitable enlargement device (e.g., a microscope, a magnifying glass, etc.) and a corresponding scale. However, it is also possible to merely compare whether or not the length l of the needle-like discoloration structures exceeds a certain reference length, for example. Further, it is possible to compare whether or not the length l of the needle-like discoloration structures falls below a certain reference length. To compensate for extreme individual length values, it is possible to analyze whether a certain subset of needle-like discoloration structures has a needle length amounting to at least a given reference length.

The achieved (measured) length l may be compared to a nominal length, which corresponds to the nominal result of photodisruption. The display of an effective energy (see below) may then be performed on the basis of this comparison.

The analysis in a view from above as well as the analysis in a side view can be performed with the help of a computer-controlled analysis device, wherein a CCD sensor or a CMOS sensor of a camera, for example, records an image of the discoloration structure, which is then analyzed in a computer-assisted process (optionally fully automatically). Further, a light source may be provided for illuminating the sample material and the discoloration structure. The light source may be configured, for example by providing suitable filters, to emit only light of a certain frequency band and/or to sequentially emit light of different frequency bands.

Next, the pulse energy of one of the sets is selected on the basis of the previous analysis. For example, the pulse energy which corresponds to the lowest set energy that has led to a complete (continuous) visible discoloration structure in the sample material 40 may be selected. To do so, the discoloration structures that are created can be compared with a reference structure (of the nominal geometric figure). Alternatively, the pulse energy which corresponds to the lowest set energy that has resulted in a discoloration structure with needle-like discoloration structures whose length exceeds a certain reference length may be selected. The two selection methods may also be combined, so that the pulse energy selected corresponds to the lowest set energy that has led to a complete (continuous) visible discoloration structure in the sample material 40 with needle-like discoloration structures, whose length l exceeds a certain reference length. The selection may be made "by hand" or by a computer and/or by a control unit of the cutting laser.

Next, a treatment pulse energy for the cutting laser is set on the basis of the selected energy. The treatment pulse energy may be set, for example, so that it corresponds to the product of the selected energy and a certain factor. If it is known, for example, that a suitable treatment pulse energy is twice as high as the selected energy, which reliably leads to a visible discoloration structure in the sample material 40, then the factor amounts to two, for example. However, the factor may also be less than one or the treatment pulse energy may be set so that there is a constant energy offset between the selected energy and the treatment pulse energy.

To facilitate the selection of the treatment pulse energy, an effective energy may be displayed for the user of the cutting laser as follows: first, a factor representing the ratio between a known reference energy for the creation of the desired discoloration structure and the selected energy is calculated. The known reference energy may be a pulse energy of the cutting laser of which it is known that under the usual conditions it leads to an adequate degree of photodisruption and/or to a continuous visible discoloration structure in the sample plate. If the selected energy deviates greatly from this reference energy, this is a sign that the usual conditions do not prevail and the cutting beam is highly defocused, for example. However, the known reference energy may also be a dimensionless value such as one, for example.

In addition, an effective energy, which corresponds to the product of an energy value currently set on the cutting laser and the factor calculated previously is also determined. The effective energy is displayed for the user of the cutting laser, so that the user is provided with an energy scale that takes into account the actual cutting performance of the cutting laser.

The step of setting the treatment pulse energy is carried out on the basis of this effective energy. The effective energy may be displayed simultaneously with a display of the set energy, for example, while the user of the cutting laser is changing the pulse energy of the cutting laser. The user of the cutting laser can be certain, on the basis of the effective energy displayed, that a certain effective energy will always lead to a reproducible cutting result on the human cornea. In other words, the displayed effective energy allows for conclusions regarding the result of photodisruption to be expected.

A brief example of the method presented above is described below. The sample material shown in FIG. 3A can be used to irradiate regions thereof using the nominal energy values indicated thereon. Analysis of the discoloration structures then yields, for example, the fact that discoloration structures which do not correspond to the nominal geometric figure because they contain gaps are present in the regions 42*a-d*. However, the regions 42*e* and 42*f* each have a discoloration structure, which corresponds to the nominal geometric figure. The energy which is the lowest energy leading to a discoloration structure, which corresponds to the nominal geometric figure is chosen as the selected energy value. In this example the selected energy thus corresponds to 0.45 µJ of the region 42e.

However, it may be known from previous investigations that under certain normal conditions (for example, with an ideally focused laser beam) an adequate discoloration structure is created in a comparable sample material (for example, PMMA) even at 0.35 µJ. The reference energy is therefore 0.35 µJ. Thus, 0.35 µJ/0.45 µJ=0.77 is calculated as the ratio between the known reference energy value and the selected energy.

Next the energy value current set on the cutting laser is multiplied times the factor 0.77 to calculate the effective energy. For example, if the energy set is 0.45 µJ, then the effective energy value 0.45 µJ*0.77=0.35 µJ is displayed as the effective energy value. The choice of the treatment pulse energy may thus be made on the basis of the effective energy because this takes into account the real conditions of the cutting laser (for example, focus, etc.).

The energy calibration according to the present invention is thus a calibration which takes into account not only the pulse energy of a cutting laser but—because actual discolorations in a sample material are analyzed—other factors, which contribute to the quality of the cut that is made and/or to the degree of photodisruption, are also taken into account.

The invention claimed is:

1. A method for energy calibration of a pulsed cutting laser for eye surgery, comprising:
   irradiating a sample material with a plurality of sets of laser pulses of the cutting laser with pulse energies differing from set to set;
   analyzing at least one visually perceptible discoloration structure created in the sample material as a result of the irradiation;
   selecting the pulse energy of one of the sets based on the analysis; and
   setting a treatment pulse energy for the cutting laser based on the selected energy.

2. The method of claim 1, wherein the sample material is transparent.

3. The method of claim 1, wherein the sets are each irradiated at different regions of the sample material.

4. The method of claim 3, wherein the different regions of the sample material are separated from one another by visible marks.

5. The method of claim 3, wherein the sample material is provided with written indications, which define a pulse energy in local assignment for each one of the regions.

6. The method of claim 3, wherein:
   a plate-like piece of material comprising PMMA is used as the sample material; and
   the sets are each irradiated at different plate regions of the piece of material.

7. The method of claim 1, wherein:
   each one of the sets corresponds to a nominal geometric figure; and
   the pulse energy of such a set is selected, at which a discoloration structure is created in the sample material, which completely represents the nominal geometric figure.

8. The method of claim 7, wherein the nominal geometric figure is or comprises a line figure.

9. The method of claim 8, wherein the line figure is closed in the form of a ring.

10. The method of claim 7, wherein the pulse energy of the set having the lowest pulse energy is selected, at which a discoloration structure is created in the sample material, which completely represents the nominal geometric figure.

11. The method of claim 1, wherein the pulse energy of such a set is selected, at which needle-like discoloration structures, which are created in the sample material as a result of the irradiation with the set, satisfying at least a certain size condition.

12. The method of claim 11, wherein the size condition is, that a needle length of the needle-like discoloration structures accounts to at least a given reference length.

13. The method of claim 11, wherein a size condition is, that at least a subset of the needle-like discoloration structures each has a needle length amounting to at least a given reference length.

14. The method of claim 1, further comprising:
   optically detecting the at least one discoloration structure by using a camera.

15. The method of claim 14, further comprising:
   displaying a camera image on a display screen, the camera image showing the at least one discoloration structure.

16. The method of claim 14, wherein analyzing comprises a software-assisted analysis of a camera image showing the at least one discoloration structure.

17. The method of claim 1, wherein the laser pulses have a pulse duration in the range of atto-, femto- or picoseconds.

18. The method of claim 1, further comprising:
   determining a measured pulse energy of the cutting laser by means of an energy meter; and
   adjusting, based on the measured pulse energy, a scale of an energy value displayed at the cutting laser as current energy, such that subsequently the energy value displayed at the cutting laser as current energy corresponds to an actual pulse energy.

19. The method of claim 1, further comprising:
   determining a ratio between a known reference energy value for the creation of a desired discoloration structure and the selected energy;
   determining an effective energy as the product of an energy value currently set as pulse energy at the cutting laser and the ratio; and
   displaying the effective energy to a user of the cutting laser, wherein the step of setting is carried out based on the effective energy.

* * * * *